(12) United States Patent  (10) Patent No.: US 8,697,706 B2
Sun et al.  (45) Date of Patent: Apr. 15, 2014

(54) COMPOUNDS FOR THE TREATMENT OF HEPATITIS C

(71) Applicant: Bristol-Myers Squibb Company, Princeton, NJ (US)

(72) Inventors: Li-Qiang Sun, Glastonbury, CT (US); Qian Zhao, Wallingford, CT (US); Paul Michael Scola, Glastonbury, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 9 days.

(21) Appl. No.: 13/628,529

(22) Filed: Sep. 27, 2012

(65) Prior Publication Data

US 2013/0095063 A1    Apr. 18, 2013

Related U.S. Application Data

(60) Provisional application No. 61/547,252, filed on Oct. 14, 2011.

(51) Int. Cl.
*C07D 498/10* (2006.01)
*C07D 498/18* (2006.01)
*A61K 31/529* (2006.01)
*A61P 31/22* (2006.01)

(52) U.S. Cl.
USPC .......................... 514/257; 540/456

(58) Field of Classification Search
USPC .......................... 514/456; 540/257
See application file for complete search history.

(56) References Cited

U.S. PATENT DOCUMENTS

| | | | |
|---|---|---|---|
| 4,816,064 A | 3/1989 | Konno et al. | |
| 7,163,943 B2 | 1/2007 | Timmer et al. | |
| 7,169,785 B2 | 1/2007 | Timmer et al. | |
| 8,445,490 B2 | 5/2013 | Wang et al. | |
| 2009/0286778 A1 | 11/2009 | Combs et al. | |
| 2011/0086858 A1 | 4/2011 | Wang et al. | |
| 2012/0093767 A1 | 4/2012 | Wang et al. | |
| 2012/0213729 A1 | 8/2012 | Sun et al. | |
| 2013/0078214 A1 | 3/2013 | Wang et al. | |
| 2013/0095066 A1 | 4/2013 | Wang et al. | |
| 2013/0203758 A1 | 8/2013 | Wang et al. | |

FOREIGN PATENT DOCUMENTS

| | | |
|---|---|---|
| KR | 2004-0033100 | 4/2004 |
| WO | WO 02/079187 | 10/2002 |
| WO | WO 2004/026881 | 4/2004 |
| WO | WO 2004/089286 | 10/2004 |
| WO | WO 2008/057209 | 5/2008 |
| WO | WO 2009/091388 | 7/2009 |
| WO | WO 2009/132202 | 10/2009 |
| WO | WO 2010/036896 | 4/2010 |
| WO | WO 2010/118367 | 10/2010 |

*Primary Examiner* — Bruck Kifle
(74) *Attorney, Agent, or Firm* — James Epperson

(57) ABSTRACT

The disclosure provides compounds of formula I, including pharmaceutically acceptable salts, as well as compositions and methods of using the compounds. The compounds have activity against hepatitis C virus (HCV) and may be useful in treating those infected with HCV.

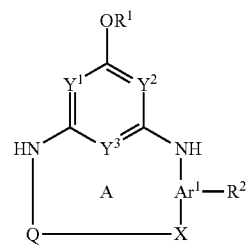

12 Claims, No Drawings

COMPOUNDS FOR THE TREATMENT OF HEPATITIS C

CROSS-REFERENCE TO RELATED APPLICATIONS

This application claims the benefit of U.S. provisional application Ser. No. 61/547,252 filed Oct. 14, 2011.

BACKGROUND OF THE INVENTION

The disclosure generally relates to the novel compounds of formula I including pharmaceutically acceptable salts, which have activity against hepatitis C virus (HCV) and are useful in treating those infected with HCV. The disclosure also relates to compositions and methods of using these compounds.

Hepatitis C virus (HCV) chronically infects an estimated 170 million people worldwide, with 3 to 4 million infected individuals in the United States alone (Boyer, N. and Marcellin, P. *J. Hepatology.* 2000, 32:98-112; Alter, M. J., et al. *Engl. J. Med.* 1999, 341:556-562). Prior to the mid 1990s, transfusion with infected blood products was the main route of HCV transmission. Following the introduction of blood screening methods, transmission via injection drug use became the primary risk factor. Chronic infection often leads to the development of severe liver complications, including fibrosis, cirrhosis, and hepatocellular carcinoma. HCV infection is also the leading cause of orthotopic liver transplantation in the United States. The degree to which disease progression is related to viral and cellular factors is not completely understood.

Considerable heterogeneity is found within the nucleotide and encoded amino acid sequence of the HCV genome (Simmonds, P. *J. Gen. Virology.* 2004, 85:3173-3188). Based on this sequence diversity, six major genotypes and multiple associated subtypes have been described. The genotypes of HCV differ in their worldwide distribution, and the clinical significance of the genetic heterogeneity of HCV remains elusive despite numerous studies of the possible effect of genotypes on pathogenesis and therapy.

Medical treatment for HCV is limited by the lack of a vaccine or approved therapies that specifically target the virus. Currently, patients undergo treatment with a combination of parenterally administered pegylated alpha-interferon and oral ribavirin. Genotype 1 HCV is the most difficult to treat and elimination of the virus (sustained virologic response) is achieved for only approximately 50% of patients (Fried, M. W. et al. *N. Engl. J. Med.* 2002, 347:975-982; Zeumzem, S. *Nature Clinical Practice.* 2008, 5:610-622). This poor treatment response, combined with often severe side effects induced by therapy, highlight a need for improved antiviral drugs with better efficacy and safety profiles.

HCV is a member of the Flaviviridae family of viruses with a single-stranded positive-sense RNA genome. Following infection of host cells, the 9.6 Kb genome is translated into a polyprotein precursor of approximately 3,000 amino acids (reviewed in Lindenbach, B. D. and Rice, C. M. *Nature.* 2005, 436:933-938; Moradpour, D, Penin, F., and Rice, C. M. *Nature Reviews.* 2007, 5:453-463). Post-translational processing by both cellular and viral proteases results in the generation of at least 10 separate viral proteins. The structural proteins (which by definition are found in mature virions) include core, E1, E2, and possibly p7, and originate from the amino-terminal region of the polyprotein. The core protein assembles into the viral nucleocapsid. The E1 and E2 glycoproteins form heterodimers that are found within the lipid envelope surrounding the viral particles, and mediate host cell receptor binding and entry of the virus into cells. It is unclear if p7 is a structural protein, and its role in replication has yet to be defined. However p7 is believed to form an ion channel in cellular membranes, preventing acidification of intracellular compartments in which virions are assembled, and it has been shown to be essential for viral replication and assembly. The nonstructural proteins NS2, NS3, NS4A, NS4B, NS5A, and NS5B are produced through maturational cleavages of the carboxy-terminal region of the polyprotein. NS2 along with the amino terminus of NS3 form the NS2-3 metalloprotease which cleaves at the NS2-NS3 junction. Additionally, NS2 is involved in assembly and egress of nascent virions. The NS3 protein contains both a serine protease in its amino-terminal region, and a nucleotide-dependent RNA helicase in its carboxy-terminal region. NS3 forms a heterodimer with the NS4A protein, constituting the active protease which mediates cleavages of the polyprotein downstream of NS3, both in cis, at the NS3-NS4A cleavage site, and in trans, for the remaining NS4A-NS4B, NS4B-NS5A, NS5A-NS5B sites. The complex formation of the NS3 protein with NS4A seems necessary to the processing events, enhancing the proteolytic efficiency at all of the sites. The NS3 protein also exhibits nucleoside triphosphatase and RNA helicase activities. The NS4B protein has been shown to be important for localization of HCV proteins into replication complexes in altered membranous structures within the cell. NS5B encodes an RNA-dependent RNA polymerase that is involved in the replication of HCV.

Subgenomic HCV replicons, containing the untranslated regions 5' and 3' to the coding sequence fused to the nonstructural proteins or the full-length polyprotein, are competent for translation, viral protein expression, and replication within cultured cells (Lohmann, V. et al. *Science.* 1999, 285:110-113; Moradpour, D, Penin, F., and Rice, C. M. *Nature Reviews.* 2007, 5:453-463). The replicon system has proven valuable for the identification of inhibitors targeting the nonstructural proteins associated with these functions. However, only limited subsets of HCV genotypes have been used to generate functional replicons.

Other systems have been used to study the biology of the HCV structural proteins that mediate the entry into host cells. For example, virus-like-particles made in recombinant baculovirus-infected cells with the HCV core, E1 and E2 proteins have also been used to study the function of the HCV E1 and E2 proteins (Barth, H., et al. *J. Biol. Chem.* 2003, 278:41003-41012). In addition, pseudotyping systems where the E1 and E2 glycoproteins are used to functionally replace the glycoproteins of retroviruses have been developed (Bartosch, B., Dubuisson, J. and Cosset, F.-L. *J. Exp. Med.* 2003, 197:633-642; Hsu, M. et al. *Proc. Natl. Acad. Sci. USA.* 2003, 100:7271-7276). These systems yield HCV pseudoparticles that bind to and enter host cells in a manner which is believed to be analogous to the natural virus, thus making them a convenient tool to study the viral entry steps as well as to identify inhibitors block this process.

Recently, a full-length genotype 2a HCV clone, JFH1, was isolated and demonstrated the ability to replicate in vitro. Through repeated passage and adaptation in cell culture increased titers of infectious virus were produced (Lindenbach, B. D., et al. *Science.* 2005, 309:623-626; Wakita, T. et al. *Nature Med.* 2005, 11:791-796). In contrast to the HCV replicon or pseudotyping systems, the infectious virus is useful for studying the complete HCV replication cycle, including identifying inhibitors of not only the replication proteins, but those involved in early steps in virus infection (entry and uncoating) and production of progeny viruses (genome packaging, nucleocapsid assembly, virion envelopment and egress).

Triazines have been disclosed. See WO 2009/091388 and US 2009/0286778.

The invention provides technical advantages, for example, the compounds are novel and are effective against hepatitis C. Additionally, the compounds provide advantages for pharmaceutical uses, for example, with regard to one or more of their mechanism of action, binding, inhibition efficacy, target selectivity, solubility, safety profiles, or bioavailability.

DESCRIPTION OF THE INVENTION

One aspect of the invention is a compound of formula I

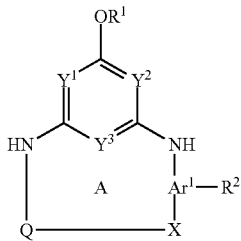

where
$Y^1$ and $Y^3$ are N and $Y^2$ is CH or $Y^2$ and $Y^3$ are N and $Y^1$ is CH;
$Ar^1$ is phenylene or pyridindiyl substituted with 1 $R^2$;
$R^1$ is alkyl, hydroxyalkyl, alkoxyalkyl, haloalkyl, cycloalkyl, hydroxycycloalkyl, alkoxycycloalkyl, halocycloalkyl, cycloalkenyl, benzyl, indanyl, or alkylcarbonyl;
$R^2$ is hydrogen, cyano, halo, alkyl, haloalkyl, alkoxy, or haloalkoxy;
$R^3$ is hydrogen, alkyl, (amino)alkyl, (alkylamino)alkyl, (dialkylamino)alkyl, ((alkylcarbonyl)amino)alkyl, ((haloalkylcarbonyl)amino)alkyl, ((alkoxycarbonyl)amino)alkyl, ((benzyloxycarbonyl)amino)alkyl, alkylcarbonyl, alkoxycarbonyl, benzyloxycarbonyl, aminocarbonyl, alkylaminocarbonyl, or dialkyaminocarbonyl;
$R^4$ is hydrogen, alkyl, (amino)alkyl, (alkylamino)alkyl, or (dialkylamino)alkyl;
$R^5$ is hydrogen, alkyl, (amino)alkyl, (alkylamino)alkyl, or (dialkylamino)alkyl;
Q is an alkylene or alkenylene chain containing 0-6 groups selected from the group consisting of O, $NR^3$, S, S(O), $S(O_2)$, C(O)O, $C(O)NR^4$, $OC(O)NR^4$, $NR^4C(O)NR^4$, and Z, provided that any O or S atom does not directly bond to another O or S atom, such that ring A is 13-36 membered; and where the alkylene or alkenylene chain is substituted with 0-6 substituents selected from the group consisting of alkyl, alkylene, hydroxy, and alkoxy;
X is O, $CH_2$, CO, $CO_2$, or $C(O)NR^5$; and
Z is $C_{3-7}$ cycloalkylene or phenylene;
or a pharmaceutically acceptable salt thereof.
Another aspect of the invention is a compound of formula I where
$Ar^1$ is phenylene or pyridindiyl substituted with 1 $R^2$;
$R^1$ is haloalkyl;
$R^2$ is hydrogen or halo;
$R^3$ is hydrogen or alkyl;
$R^5$ is hydrogen or alkyl;
Q is an alkylene or alkenylene chain containing 0-6 groups selected from the group consisting of O, $NR^3$, and Z, provided that any O atom does not directly bond to another O atom, such that ring A is 13-36 membered; and where the alkylene or alkenylene chain is substituted with 0-6 substituents selected from the group consisting of alkyl and alkylene;
X is $C(O)NR^5$; and
Z is $C_{3-7}$ cycloalkylene or phenylene;
or a pharmaceutically acceptable salt thereof.
Another aspect of the invention is a compound of formula I where
$Ar^1$ is 1,4-phenylene or 1,4-dipyridindiyl substituted with 1 $R^2$;
$R^1$ is trifluoroethyl;
$R^2$ is hydrogen or fluoro;
$R^3$ is hydrogen;
$R^5$ is hydrogen;
Q is an alkylene or alkenylene chain containing 0-6 groups selected from the group consisting of O, $NR^3$, and Z, provided that any O atom does not directly bond to another O atom, such that ring A is 13-36 membered; and where the alkylene or alkenylene chain is substituted with 0-6 substituents selected from the group consisting of methyl and methylene;
X is $C(O)NR^5$; and
Z is $C_{3-7}$ cycloalkylene or phenylene;
or a pharmaceutically acceptable salt thereof.
Another aspect of the invention is a compound of formula I where ring A is 13-36 membered.
Another aspect of the invention is a compound of formula I where ring A is 20-30 membered.
Another aspect of the invention is a compound of formula I where ring A is 23-24 membered.
Another aspect of the invention is a compound of formula I where $Ar^1$ is 1,4-benzenediyl substituted with 1 $R^2$; or a pharmaceutically acceptable salt thereof.
Another aspect of the invention is a compound of formula I where $Ar^1$ is 1,4-dipyridindiyl substituted with 1 $R^2$; or a pharmaceutically acceptable salt thereof.
Another aspect of the invention is a compound of formula I where Z is 1,4-phenylene; or a pharmaceutically acceptable salt thereof.
Another aspect of the invention is a compound of formula I where Z is cyclopropylene; or a pharmaceutically acceptable salt thereof.

Any scope of any variable, including $R^1$, $R^2$, $R^3$, $R^4$, $R^5$, $Ar^1$, Q, X, and Z, can be used independently with the scope of any other instance of a variable.

Unless specified otherwise, these terms have the following meanings. "Halo" means fluoro, chloro, bromo, or iodo. "Alkyl" means a straight or branched alkyl group composed of 1 to 6 carbons. "Alkenyl" means a straight or branched alkyl group composed of 2 to 6 carbons with at least one double bond. "Cycloalkyl" means a monocyclic ring system composed of 3 to 7 carbons. "Alkylene" means a straight or branched divalent alkyl group composed of 2 to 36 carbons. "Alkenylene" means a straight or branched divalent alkyl group composed of 2 to 36 carbons with at least one double bond. For ring A, Y is an alkylene or alkenylene chain with sufficient carbons and optionally other defined groups to form a 13-36 membered ring. "Cycloalkylene" means a divalent cycloalkane moiety composed of 3 to 7 carbons and includes gem-divalency (for example 1,1-cyclopropanediyl) as well as non-gem-divalency (for example, 1,4-cyclohexanediyl). "Alkylidinyl" means a divalent alkene substituent where the divalency occurs on the same carbon of the alkene. "Hydroxyalkyl," "alkoxy" and other terms with a substituted alkyl moiety include straight and branched isomers composed of 1 to 6 carbon atoms for the alkyl moiety. "Haloalkyl" and "haloalkoxy" include all halogenated isomers from monohalo substituted alkyl to perhalo substituted alkyl. "Aryl" includes carbocyclic and heterocyclic aromatic substituents. Phenylene is a divalent benzene ring. $Ar^1$ is a divalent heteroaryl ring with respect to forming ring A as in formula I with the substituent $R^2$. "1,4-Phenylene" means 1,4-benzenediyl with respect to regiochemistry for the divalent moiety. Parenthetic and multiparenthetic terms are intended to clarify bonding relationships to those skilled in the art. For example, a term such as ((R)alkyl) means an alkyl substituent further substituted with the substituent R.

The substituents described above may be attached at any suitable point of attachment unless otherwise specified. However, it is understood that the compounds encompassed by the present invention are those that are chemically stable as understood by those skilled in the art. Additionally, the compounds encompassed by the present disclosure are those that are suitably stable for use as a pharmaceutical agent.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, camsylate, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention possess asymmetric carbon atoms (see, for example, the structures below). The invention includes all stereoisomeric forms, including enantiomers and diastereomers as well as mixtures of stereoisomers such as racemates. Some stereoisomers can be made using methods known in the art. Stereoisomeric mixtures of the compounds and related intermediates can be separated into individual isomers according to methods commonly known in the art. The use of wedges or hashes in the depictions of molecular structures in the following schemes and tables is intended only to indicate relative stereochemistry, and should not be interpreted as implying absolute stereochemical assignments.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Biological Methods

Infection assays. HCV pseudoparticles, produced using standardized methodology (Bartosch, B., Dubuisson, J. and Cosset, F.-L. *J. Exp. Med.* 2003, 197:633-642) were made via a liposome-based transfection procedure of 293T cells with plasmids expressing the murine leukemia virus capsid and polymerase proteins, an MLV genome encoding the luciferase reporter gene, and envelope glycoproteins from either HCV or vesicular stomatitis virus (VSV). The genotype 1a HCV E1 and E2 envelope coding sequences were derived from the H77C isolate (GenBank accession number AF009606). Media containing pseudoparticles was collected 3 days following transfection, filtered, and stored at −20° C. as a viral stock. Infections were performed in 384-well plates by mixing pseudovirus with $1 \times 10^4$ Huh7 cells/well in the presence or absence of test inhibitors, followed by incubation at 37° C. Luciferase activity, reflecting the degree of entry of the pseudoparticles into host cells, was measured 2 days after infection. The specificity of the compounds for inhibiting HCV was determined by evaluating inhibition of VSV pseudoparticle infection.

Compounds and data analysis. Test compounds were serially diluted 3-fold in dimethyl sulfoxide (DMSO) to give a final concentration range in the assay of 50.0 µM to 0.04 pM. Maximum activity (100% of control) and background were derived from control wells containing DMSO but no inhibitor or from uninfected wells, respectively. The individual signals in each of the compound test wells were then divided by the averaged control values after background subtraction and multiplied by 100% to determine percent activity. Assays were performed in duplicate and average $EC_{50}$ values (reflecting the concentration at which 50% inhibition of virus replication was achieved) were calculated. Compound $EC_{50}$ data is expressed as A:=≤100 nM; B=100-1000 nM. Representative data for compounds are reported in Table 1.

TABLE 1

| Number | Structure | $EC_{50}$ (nM) | $EC_{50}$ (nM) |
|---|---|---|---|
| 3001 | 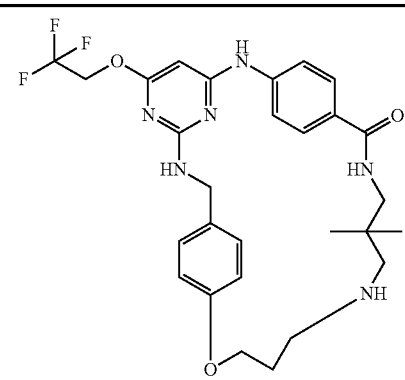 | 106 | B |
| 3002 | 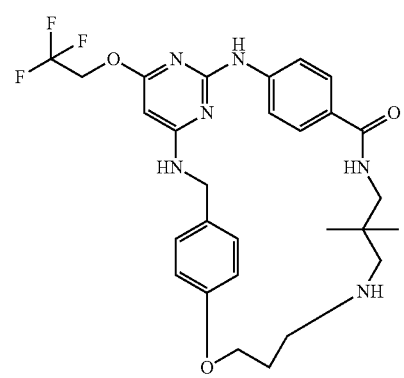 [SMILES: CC1(C)CNCCCOc2ccc(cc2)CNc2cc(OCC(F)(F)F)nc(n2)Nc2ccc(cc2)C(=O)NC1] | | A |

Pharmaceutical Compositions and Methods of Treatment

The compounds demonstrate activity against HCV NS5B and can be useful in treating HCV and HCV infection. Therefore, another aspect of the invention is a composition comprising a compound, or a pharmaceutically acceptable salt thereof, and a pharmaceutically acceptable carrier.

Another aspect of the invention is a composition further comprising a compound having anti-HCV activity.

Another aspect of the invention is a composition where the compound having anti-HCV activity is an interferon or a ribavirin. Another aspect of the invention is where the interferon is selected from interferon alpha 2B, pegylated interferon alpha, consensus interferon, interferon alpha 2A, interferon lambda, and lymphoblastoid interferon tau.

Another aspect of the invention is a composition where the compound having anti-HCV activity is a cyclosporin. Another aspect of the invention is where the cyclosporin is cyclosporin A.

Another aspect of the invention is a composition where the compound having anti-HCV activity is selected from the group consisting of interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is a composition where the compound having anti-HCV activity is effective to inhibit the function of a target selected from HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is a composition comprising a compound, or a pharmaceutically acceptable salt thereof, a pharmaceutically acceptable carrier, an interferon and ribavirin.

Another aspect of the invention is a method of inhibiting the function of the HCV replicon comprising contacting the HCV replicon with a compound or a pharmaceutically acceptable salt thereof.

Another aspect of the invention is a method of inhibiting the function of the HCV NS5B protein comprising contacting the HCV NS5B protein with a compound or a pharmaceutically acceptable salt thereof.

Another aspect of the invention is a method of treating an HCV infection in a patient comprising administering to the patient a therapeutically effective amount of a compound or a pharmaceutically acceptable salt thereof. In another embodiment the compound is effective to inhibit the function of the HCV replicon. In another embodiment the compound is effective to inhibit the function of the HCV NS5B protein.

Another aspect of the invention is a method of treating an HCV infection in a patient comprising administering to the patient a therapeutically effective amount of a compound, or a pharmaceutically acceptable salt thereof, in conjunction with (prior to, after, or concurrently) another compound having anti-HCV activity.

Another aspect of the invention is the method where the other compound having anti-HCV activity is an interferon or a ribavirin.

Another aspect of the invention is the method where the interferon is selected from interferon alpha 2B, pegylated interferon alpha, consensus interferon, interferon alpha 2A, interferon lambda, and lymphoblastoid interferon tau.

Another aspect of the invention is the method where the other compound having anti-HCV activity is a cyclosporin.

Another aspect of the invention is the method where the cyclosporin is cyclosporin A.

Another aspect of the invention is the method where the other compound having anti-HCV activity is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is the method where the other compound having anti-HCV activity is effective to inhibit the function of a target selected from the group consisting of HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is the method where the other compound having anti-HCV activity is effective to inhibit the function of target in the HCV life cycle other than the HCV NS5B protein.

"Therapeutically effective" means the amount of agent required to provide a meaningful patient benefit as understood by practitioners in the field of hepatitis and HCV infection.

"Patient" means a person infected with the HCV virus and suitable for therapy as understood by practitioners in the field of hepatitis and HCV infection.

"Treatment," "therapy," "regimen," "HCV infection," and related terms are used as understood by practitioners in the field of hepatitis and HCV infection.

The compounds of this invention are generally given as pharmaceutical compositions comprised of a therapeutically effective amount of a compound or its pharmaceutically acceptable salt and a pharmaceutically acceptable carrier and may contain conventional excipients. Pharmaceutically acceptable carriers are those conventionally known carriers having acceptable safety profiles. Compositions encompass all common solid and liquid forms including for example capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions. See, for example, *Remington's Pharmaceutical Sciences*, Mack Publishing Company, Easton, PA, 17th edition, 1985.

Solid compositions are normally formulated in dosage units and compositions providing from about 1 to 1000 mg of the active ingredient per dose are preferred.

Some examples of dosages are 1 mg, 10 mg, 100 mg, 250 mg, 500 mg, and 1000 mg. Generally, other agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other agents will be present in a unit range similar to agents of that class used clinically. Typically, this is 1-100 mg/mL.

The invention encompasses all conventional modes of administration; oral and parenteral methods are preferred. Generally, the dosing regimen will be similar to other agents used clinically. Typically, the daily dose will be 1-100 mg/kg body weight daily. Generally, more compound is required orally and less parenterally. The specific dosing regime, however, will be determined by a physician using sound medical judgement.

The invention also encompasses methods where the compound is given in combination therapy. That is, the compound can be used in conjunction with, but separately from, other agents useful in treating hepatitis and HCV infection. In these combination methods, the compound will generally be given in a daily dose of 1-100 mg/kg body weight daily in conjunction with other agents. The other agents generally will be given in the amounts used therapeutically. The specific dosing regime, however, will be determined by a physician using sound medical judgement.

Some examples of compounds suitable for compositions and methods are listed in Table 2.

TABLE 2

| Brand Name | Physiological Class | Type of Inhibitor or Target | Source Company |
|---|---|---|---|
| NIM811 | | Cyclophilin Inhibitor | Novartis |
| Zadaxin | | Immuno-modulator | Sciclone |
| Suvus | | Methylene blue | Bioenvision |
| Actilon (CPG10101) | | TLR9 agonist | Coley |
| Batabulin (T67) | Anticancer | β-tubulin inhibitor | Tularik Inc., South San Francisco, CA |
| ISIS 14803 | Antiviral | antisense | ISIS Pharmaceuticals Inc, Carlsbad, CA/Elan Phamaceuticals Inc., New York, NY |
| Summetrel | Antiviral | antiviral | Endo Pharmaceuticals Holdings Inc., Chadds Ford, PA |
| GS-9132 (ACH-806) | Antiviral | HCV Inhibitor | Achillion/Gilead |
| Pyrazolopyrimidine compounds and salts From WO-2005047288 26 May 2005 | Antiviral | HCV Inhibitors | Arrow Therapeutics Ltd. |
| Levovirin | Antiviral | IMPDH inhibitor | Ribapharm Inc., Costa Mesa, CA |
| Merimepodib (VX-497) | Antiviral | IMPDH inhibitor | Vertex Pharmaceuticals Inc., Cambridge, MA |
| XTL-6865 (XTL-002) | Antiviral | monoclonal antibody | XTL Biopharmaceuticals Ltd., Rehovot, Isreal |
| Telaprevir (VX-950, LY-570310) | Antiviral | NS3 serine protease inhibitor | Vertex Pharmaceuticals Inc., Cambridge, MA/Eli Lilly and Co. Inc., Indianapolis, IN |
| HCV-796 | Antiviral | NS5B Replicase Inhibitor | Wyeth/Viropharma |
| NM-283 | Antiviral | NS5B Replicase Inhibitor | Idenix/Novartis |
| GL-59728 | Antiviral | NS5B Replicase Inhibitor | Gene Labs/Novartis |
| GL-60667 | Antiviral | NS5B Replicase Inhibitor | Gene Labs/Novartis |
| 2'C MeA | Antiviral | NS5B Replicase Inhibitor | Gilead |
| PSI 6130 | Antiviral | NS5B Replicase Inhibitor | Roche |
| R1626 | Antiviral | NS5B Replicase Inhibitor | Roche |
| 2'C Methyl adenosine | Antiviral | NS5B Replicase Inhibitor | Merck |
| JTK-003 | Antiviral | RdRp inhibitor | Japan Tobacco Inc., Tokyo, Japan |
| Levovirin | Antiviral | ribavirin | ICN Pharmaceuticals, Costa Mesa, CA |
| Ribavirin | Antiviral | ribavirin | Schering-Plough Corporation, Kenilworth, NJ |
| Viramidine | Antiviral | Ribavirin Prodrug | Ribapharm Inc., Costa Mesa, CA |

TABLE 2-continued

| Brand Name | Physiological Class | Type of Inhibitor or Target | Source Company |
|---|---|---|---|
| Heptazyme | Antiviral | ribozyme | Ribozyme Pharmaceuticals Inc., Boulder, CO |
| BILN-2061 | Antiviral | serine protease inhibitor | Boehringer Ingelheim Pharma KG, Ingelheim, Germany |
| SCH 503034 | Antiviral | serine protease inhibitor | Schering Plough |
| Zadazim | Immune modulator | Immune modulator | SciClone Pharmaceuticals Inc., San Mateo, CA |
| Ceplene | Immunomodulator | immune modulator | Maxim Pharmaceuticals Inc., San Diego, CA |
| CellCept | Immunosuppressant | HCV IgG immuno-suppressant | F. Hoffmann-La Roche LTD, Basel, Switzerland |
| Civacir | Immunosuppressant | HCV IgG immuno-suppressant | Nabi Biopharmaceuticals Inc., Boca Raton, FL |
| Albuferon-α | Interferon | albumin IFN-α2b | Human Genome Sciences Inc., Rockville, MD |
| Infergen A | Interferon | IFN alfacon-1 | InterMune Pharmaceuticals Inc., Brisbane, CA |
| Omega IFN | Interferon | IFN-ω | Intarcia Therapeutics |
| IFN-β and EMZ701 | Interferon | IFN-β and EMZ701 | Transition Therapeutics Inc., Ontario, Canada |
| Rebif | Interferon | IFN-β1a | Serono, Geneva, Switzerland |
| Roferon A | Interferon | IFN-α2a | F. Hoffmann-La Roche LTD, Basel, Switzerland |
| Intron A | Interferon | IFN-α2b | Schering-Plough Corporation, Kenilworth, NJ |
| Intron A and Zadaxin | Interferon | IFN-α2b/α1-thymosin | RegeneRx Biopharma. Inc., Bethesda, MD/ SciClone Pharmaceuticals Inc, San Mateo, CA |
| Rebetron | Interferon | IFN-α2b/ribavirin | Schering-Plough Corporation, Kenilworth, NJ |
| Actimmune | Interferon | INF-γ | InterMune Inc., Brisbane, CA |
| Interferon-β | Interferon | Interferon-β-1a | Serono |
| Multiferon | Interferon | Long lasting IFN | Viragen/ Valentis |
| Wellferon | Interferon | Lympho-blastoid IFN-αn1 | GlaxoSmithKline plc, Uxbridge, UK |
| Omniferon | Interferon | natural IFN-α | Viragen Inc., Plantation, FL |
| Pegasys | Interferon | PEGylated IFN-α2a | F. Hoffmann-La Roche LTD, Basel, Switzerland |
| Pegasys and Ceplene | Interferon | PEGylated IFN-α2a/ immune modulator | Maxim Pharmaceuticals Inc., San Diego, CA |
| Pegasys and Ribavirin | Interferon | PEGylated IFN-α2a/ribavirin | F. Hoffmann-La Roche LTD, Basel, Switzerland |
| PEG-Intron | Interferon | PEGylated IFN-α2b | Schering-Plough Corporation, Kenilworth, NJ |
| PEG-Intron/ Ribavirin | Interferon | PEGylated IFN-α2b/ribavirin | Schering-Plough Corporation, Kenilworth, NJ |
| IP-501 | Liver protection | antifibrotic | Indevus Pharmaceuticals Inc., Lexington, MA |

TABLE 2-continued

| Brand Name | Physiological Class | Type of Inhibitor or Target | Source Company |
|---|---|---|---|
| IDN-6556 | Liver protection | caspase inhibitor | Idun Pharmaceuticals Inc., San Diego, CA |
| ITMN-191 (R-7227) | Antiviral | serine protease inhibitor | InterMune Pharmaceuticals Inc., Brisbane, CA |
| GL-59728 | Antiviral | NS5B Replicase Inhibitor | Genelabs |
| ANA-971 | Antiviral | TLR-7 agonist | Anadys |
| Boceprevir | Antiviral | serine protease inhibitor | Schering Plough |
| TMS-435 | Antiviral | serine protease inhibitor | Tibotec BVBA, Mechelen, Belgium |
| BI-201335 | Antiviral | serine protease inhibitor | Boehringer Ingelheim Pharma KG, Ingelheim, Germany |
| MK-7009 | Antiviral | serine protease inhibitor | Merck |
| PF-00868554 | Antiviral | replicase inhibitor | Pfizer |
| ANA598 | Antiviral | Non-Nucleoside NS5B Polymerase Inhibitor | Anadys Pharmaceuticals, Inc., San Diego, CA, USA |
| IDX375 | Antiviral | Non-Nucleoside Replicase Inhibitor | Idenix Pharmaceuticals, Cambridge, MA, USA |
| BILB 1941 | Antiviral | NS5B Polymerase Inhibitor | Boehringer Ingelheim Canada Ltd R&D, Laval, QC, Canada |
| PSI-7851 | Antiviral | Nucleoside Polymerase Inhibitor | Pharmasset, Princeton, NJ, USA |
| PSI-7977 | Antiviral | Nucleotide NS5B Polymerase Inhibitor | Pharmasset, Princeton, NJ, USA |
| VCH-759 | Antiviral | NS5B Polymerase Inhibitor | ViroChem Pharma |
| VCH-916 | Antiviral | NS5B Polymerase Inhibitor | ViroChem Pharma |
| GS-9190 | Antiviral | NS5B Polymerase Inhibitor | Gilead |
| Peg-interferon lamda | Antiviral | Interferon | ZymoGenetics/ Bristol-Myers Squibb |

Synthetic Methods

The compounds may be made by methods known in the art including those described below and including variations within the skill of the art. Some reagents and intermediates are known in the art. Other reagents and intermediates can be made by methods known in the art using readily available materials. The variables (e.g. numbered "R" substituents) used to describe the synthesis of the compounds are intended only to illustrate how to make the compounds and are not to be confused with variables used in the claims or in other sections of the specification. The following methods are for illustrative purposes and are not intended to limit the scope of the invention.

Abbreviations used in the schemes generally follow conventions used in the art. Chemical abbreviations used in the specification and examples are defined as follows: "NaHMDS" for sodium bis(trimethylsilyl)amide; "DMF" for N,N-dimethylformamide; "MeOH" for methanol; "NBS" for N-bromosuccinimide; "Ar" for aryl; "TFA" for trifluoroacetic acid; "LAH" for lithium aluminum hydride; "BOC", "DMSO" for dimethylsulfoxide; "h" for hours; "rt" for room temperature or retention time (context will dictate); "min" for minutes; "EtOAc" for ethyl acetate; "THF" for tetrahydrofuran; "EDTA" for ethylenediaminetetraacetic acid; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; "DIEA" for diisopropylethylamine, "Nf" for CF$_3$(CF$_2$)$_3$SO$_2$—; and "TMOF" for trimethylorthoformate.

Abbreviations are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Synthetic Methods

LC/MS Method (i.e., compound identification). Liquid chromatography (LC)/mass spectra (MS) were run on a Shimadzu LC instrument coupled to a Water Micromass ZQ instrument and the LCMS conditions are shown in the table. The Mass Spectrometry (MS) data were determined with a Micromass Platform for LC in electrospray mode.

EXAMPLE 3001

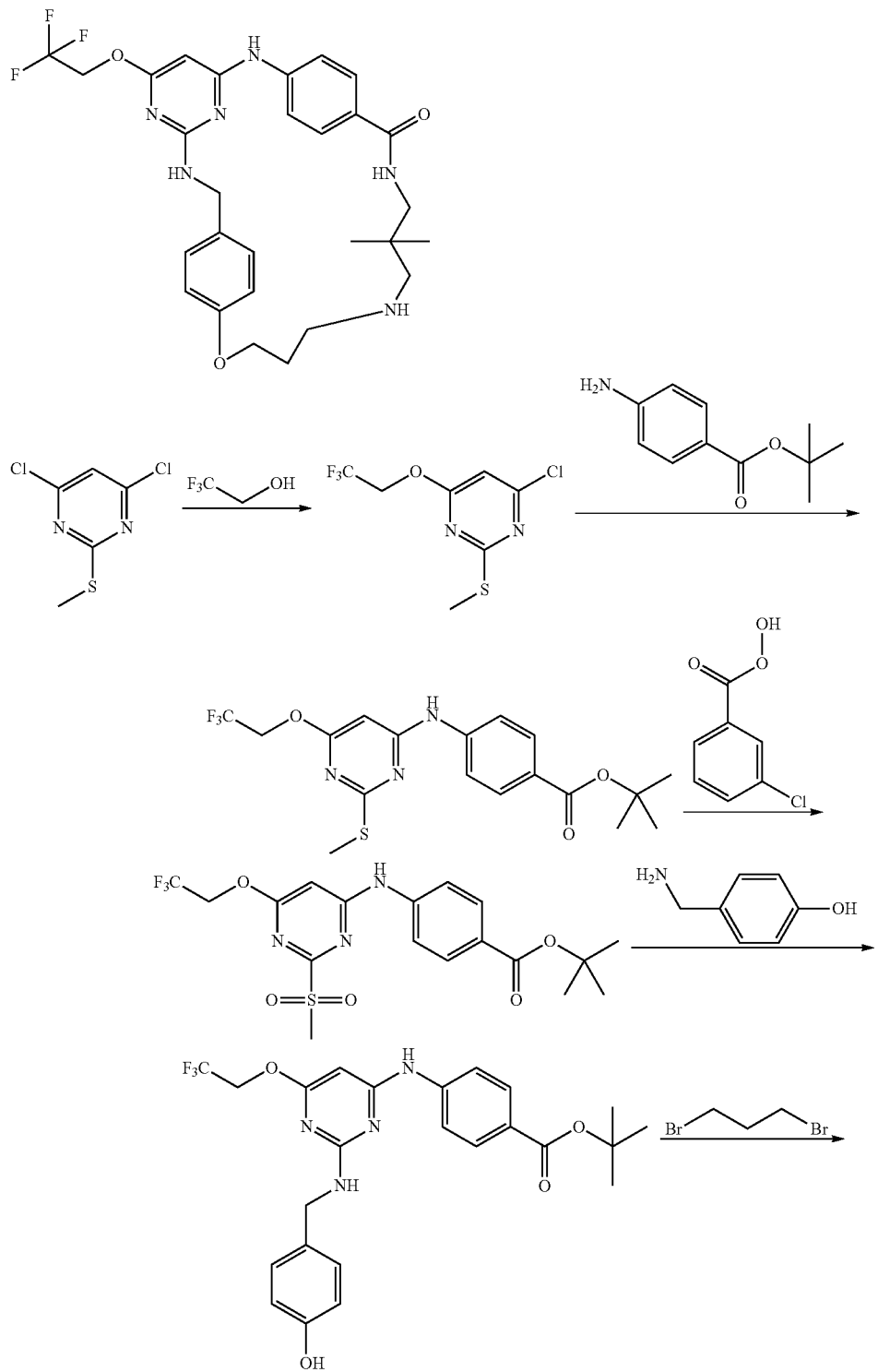

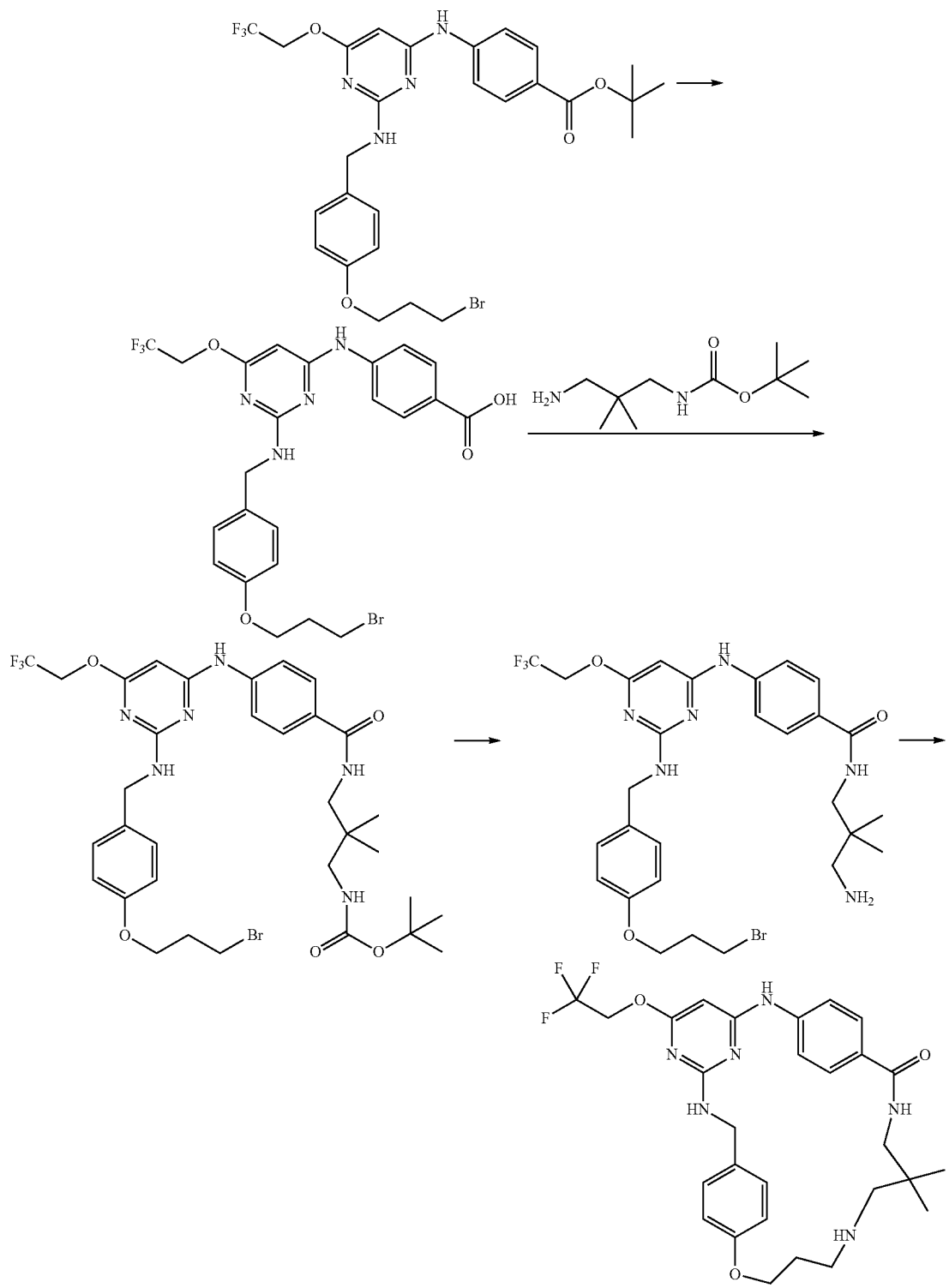

Step 1: To a solution of NaH (0.57 g, 14.35 mmol) in THF (10 mL) at 0° C. was added 2,2,2-trifluoroethanol (1.231 g, 12.30 mmol) dropwise. The mixture was stirred at 0° C. for 10 mins. The resulting mixture was transferred to the solution of 4,6-dichloro-2-(methylthio)pyrimidine (2 g, 10.25 mmol) in THF at 0° C. dropwise. Run the reaction for 16 hs at r.t. The reaction mixture was quenched with water, extracted with ethyl acetate, dried over $Na_2SO_4$, concentrated to give a crude product (3 g) that was used in the next step without purification.

| 4-chloro-2-(methylthio)-6-(2,2,2-trifluoroethoxy)pyrimidine | |
| --- | --- |
| MS (M + H)+ Calcd. | 259.6 |
| MS (M + H)+ Observ. | 259.0 |
| Retention Time | 2.16 min |
| LC Condition | |
| Solvent A | 95% Water-5% Methanol-10 mM Ammonium Actetate |
| Solvent B | 5% Water-95% Methanol-10 mM Ammonium Actetate |
| Start % B | 0 |
| Final % B | 100 |
| Gradient/Stop Time | 2 min/3 min |
| Flow Rate | 1 mL/min |
| Wavelength | 220 |
| Solvent Pair | Water-Methanol-Ammonium Actetate |
| Column | PHENOMENEX-LUNA 2.0 × 30 mm C18 3 μM |

Step 2: To a mixture of 4-chloro-2-(methylthio)-6-(2,2,2-trifluoroethoxy)pyrimidine (200 mg, 0.77 mmol) and tert-butyl 4-aminobenzoate (179 mg, 0.93 mmol) in THF (5 mL) solution was added sodium bis(trimethylsilyl)amide 1 M in THF (1.55 mL, 1.55 mmol) solution. The resulting mixture was stirred at r.t for 16 h. The reaction mixture was quenched with water, extracted with ethyl acetate, dried over MgSO4, concentrated to give a crude material that was purified by Biotage eluting with 20% then 40% to 60% of ethyl acetate/hexane to give 100 mg (31%) of the desired product as a solid.

| tert-butyl 4-((2-(methylthio)-6-(2,2,2-trifluoroethoxy)pyrimidin-4-yl)amino)benzoate | |
| --- | --- |
| MS (M + H)+ Calcd. | 416.1 |
| MS (M + H)+ Observ. | 416.1 |
| Retention Time | 2.42 min |
| LC Condition | |
| Solvent A | 95% Water-5% Methanol-10 mM Ammonium Actetate |
| Solvent B | 5% Water-95% Methanol-10 mM Ammonium Actetate |
| Start % B | 0 |
| Final % B | 100 |
| Gradient/Stop Time | 2 min/3 min |
| Flow Rate | 1 mL/min |
| Wavelength | 220 |
| Solvent Pair | Water-Methanol-Ammonium Actetate |
| Column | PHENOMENEX-LUNA 2.0 × 30 mm C18 3 μM |

Step 3: To a suspension of tert-butyl 4-((2-(methylthio)-6-(2,2,2-trifluoroethoxy)pyrimidin-4-yl)amino)benzoate (100 mg, 0.290 mmol) in DCM (5 mL) was added 3-chlorobenzoperoxoic acid (135 mg, 0.60 mmol) at 0° C. The mixture was stirred at r.t for 16 hs. The reaction mixture was concentrated to give a crude material that was purified by Biotage eluting with 20% then 40% of ethyl acetate/hexane to give 88 mg (82%) of the desired product as a solid.

| tert-butyl 4-((2-(methylsulfonyl)-6-(2,2,2-trifluoroethoxy)pyrimidin-4-yl)amino)benzoate | |
| --- | --- |
| MS (M + H)+ Calcd. | 448.4 |
| MS (M + H)+ Observ. | 448.2 |
| Retention Time | 2.18 min |
| LC Condition | |
| Solvent A | 95% Water-5% Methanol-10 mM Ammonium Actetate |
| Solvent B | 5% Water-95% Methanol-10 mM Ammonium Actetate |
| Start % B | 0 |
| Final % B | 100 |
| Gradient/Stop Time | 2 min/3 min |
| Flow Rate | 1 mL/min |
| Wavelength | 220 |
| Solvent Pair | Water-Methanol-Ammonium Actetate |
| Column | PHENOMENEX-LUNA 2.0 × 30 mm C18 3 μM |

Step 4: To a solution of tert-butyl 4-((2-(methylsulfonyl)-6-(2,2,2-trifluoroethoxy)pyrimidin-4-yl)amino)benzoate (80 mg, 0.18 mmol), and Hunig's Base (0.062 mL, 0.36 mmol) in THF (1 mL) was added 4-(aminomethyl)phenol (44 mg, 0.36 mmol). The resulting mixture was stirred at r.t for 16 hs. The solvent was removed and the crude product was purified by silica gel chromatography using 40-70%-100% EtOAc/Hexanes to give tert-butyl 4-((2-((4-hydroxybenzyl)amino)-6-(2,2,2-trifluoroethoxy)pyrimidin-4-yl)amino)benzoate (72 mg, 83%) as white solid.

| tert-butyl 4-((2-((4-hydroxybenzyl)amino)-6-(2,2,2-trifluoroethoxy)-pyrimidin-4-yl)amino)benzoate | |
| --- | --- |
| MS (M + H)+ Calcd. | 491.2 |
| MS (M + H)+ Observ. | 491.4 |
| Retention Time | 1.04 min |
| LC Condition | |
| Solvent A | 100% Water: 0.05% TFA |
| Solvent B | 100% ACN: 0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN:Water:TFA |
| Column | Acquity UPLC BEH C18 1.7 μm |

Step 5: To a solution of tert-butyl 4-((2-((4-hydroxybenzyl)amino)-6-(2,2,2-trifluoroethoxy)pyrimidin-4-yl)amino)benzoate (72 mg, 0.15 mmol), 1,3-dibromopropane (89 mg, 0.44 mmol) in acetone (1 mL) was added potassium carbonate (61 mg, 0.44 mmol). The resulting solution was stirred for 16 h at reflux. After cooling to rt, the solvent was removed and the crude product was purified by Biotage eluting with 20-40% ethyl acetate in hexane to give tert-butyl 4-((2-((4-(3-bromopropoxy)benzyl)amino)-6-(2,2,2-trifluoroethoxy)pyrimidin-4-yl)amino)benzoate (36 mg, 40%) as white solid.

| tert-butyl 4-((2-((4-(3-bromopropoxy)benzyl)amino)-6-(2,2,2-trifluoroethoxy)pyrimidin-4-yl)amino)benzoate | |
| --- | --- |
| MS (M + H)+ Calcd. | 612.5 |
| MS (M + H)+ Observ. | 612.1 |
| Retention Time | 1.19 min |
| LC Condition | |
| Solvent A | 100% Water: 0.05% TFA |
| Solvent B | 100% ACN: 0.05% TFA |
| Start % B | 2 |
| Final % B | 98 |
| Gradient Time | 2.2 min |
| Flow Rate | 0.8 mL/min |

| tert-butyl 4-((2-((4-(3-bromopropoxy)benzyl)amino)-6-(2,2,2-trifluoroethoxy)pyrimidin-4-yl)amino)benzoate | |
| --- | --- |
| Wavelength | 220 |
| Solvent Pair | ACN: Water: TFA |
| Column | Acquity UPLC BEH C18 1.7 µm |

Step 6: Tert-butyl 4-((2-((4-(3-bromopropoxy)benzyl)amino)-6-(2,2,2-trifluoroethoxy)pyrimidin-4-yl)amino)benzoate (36 mg, 0.06 mmol) and 4 N HCl in dioxane (1 mL) were stirred for 8 hs then concentrated under vacuum to give 4-((2-((4-(3-bromopropoxy)benzyl)amino)-6-(2,2,2-trifluoroethoxy)pyrimidin-4-yl)amino)benzoic acid which was carried to the next step without purification.

| 4-((2-((4-(3-bromopropoxy)benzyl)amino)-6-(2,2,2-trifluoroethoxy)pyrimidin-4-yl)amino)benzoic acid | |
| --- | --- |
| MS (M + H)$^+$ Calcd. | 556.3 |
| MS (M + H)$^+$ Observ. | 556.0 |
| Retention Time | 1.03 min |
| LC Condition | |
| Solvent A | 100% Water: 0.05% TFA |
| Solvent B | 100% ACN: 0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN: Water: TFA |
| Column | Acquity UPLC BEH C18 1.7 µm |

Step 7: To a solution of 4-((2-((4-(3-bromopropoxy)benzyl)amino)-6-(2,2,2-trifluoroethoxy)pyrimidin-4-yl)amino)benzoic acid (33 mg, 0.06 mmol), Hunig's Base (0.052 mL, 0.30 mmol) and tert-butyl (3-amino-2,2-dimethylpropyl)carbamate (23.9 mg, 0.12 mmol) in CH$_2$Cl$_2$ (2 mL) was added HATU (34 mg, 0.09 mmol). After stirring at room temperature for 1 h, the mixture was concentrated and purified by Biotage eluting with 50-70% ethyl acetate in hexane to give 35 mg of product (80%) as a white solid.

| tert-butyl (3-(4-((2-((4-(3-bromopropoxy)-benzyl)-amino)-6-(2,2,2-trifluoroethoxy)pyrimidin-4-yl)-amino)-benzamido)-2,2-dimethylpropyl)carbamate | |
| --- | --- |
| MS (M + H)$^+$ Calcd. | 740.6 |
| MS (M + H)$^+$ Observ. | 741.3 |
| Retention Time | 1.13 min |
| LC Condition | |
| Solvent A | 100% Water: 0.05% TFA |
| Solvent B | 100% ACN: 0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN: Water: TFA |
| Column | Acquity UPLC BEH C18 1.7 µm |

Step 8: tert-butyl (3-(4-((2-((4-(3-bromopropoxy)benzyl)amino)-6-(2,2,2-trifluoroethoxy)pyrimidin-4-yl)amino)benzamido)-2,2-dimethylpropyl)carbamate (35 mg, 0.047 mmol) was stirred in TFA/DCM (1:1) solution (2 mL) for 1 h. The solution was concentrated and free TFA to give N-(3-amino-2,2-dimethylpropyl)-4-((2-((4-(3-bromopropoxy)benzyl)amino)-6-(2,2,2-trifluoroethoxy)pyrimidin-4-yl)amino)benzamide which was carried to the next step without purification.

| N-(3-amino-2,2-dimethylpropyl)-4-((2-((4-(3-bromopropoxy)benzyl)amino)-6-(2,2,2-trifluoroethoxy)pyrimidin-4-yl)amino)benzamide | |
| --- | --- |
| MS (M + H)$^+$ Calcd. | 640.5 |
| MS (M + H)$^+$ Observ. | 640.2 |
| Retention Time | 0.94 min |
| LC Condition | |
| Solvent A | 100% Water: 0.05% TFA |
| Solvent B | 100% ACN: 0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN: Water: TFA |
| Column | Acquity UPLC BEH C18 1.7 µm |

Step 9: To a solution of N-(3-amino-2,2-dimethylpropyl)-4-((2-((4-(3-bromopropoxy)benzyl)amino)-6-(2,2,2-trifluoroethoxy)pyrimidin-4-yl)amino)benzamide (30 mg, 0.06 mmol) in ACN (2 mL) was added potassium carbonate (15 mg, 0.10 mmol). The mixture was heated in microwave reactor at 130° C. for 1 h. After cooling to rt, the mixture was filtered and white solid was washed with ACN. Pre-HPLC separation to give Compound 3001 (5.5 mg, 13%) as white solid.

$^1$H NMR (400 MHz, METHANOL-d$_4$) δ 7.42 (d, J=9.0 Hz, 2H), 7.36 d, J=9.3 Hz, 2H), 7.26 (d, J=8.8 Hz, 2H), 6.97 (d, J=8.5 Hz, 2H), 5.0 (s, 1H), 4.87 (t, 2H), 4.58 (s, 2H), 4.42 (t, J=5.8 Hz, 2H), 3.37 (s, 2H), 3.13 (t, J=6.0 Hz, 2H), 2.72 (s, 2H), 2.35-2.20 (m, 2H), 1.11 (s, 6H).

| Compound 3001 | |
| --- | --- |
| MS (M + H)$^+$ Calcd. | 559.6 |
| MS (M + H)$^+$ Observ. | 559.2 |
| Retention Time | 0.88 min |
| LC Condition | |
| Solvent A | 100% Water: 0.05% TFA |
| Solvent B | 100% ACN: 0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN: Water: TFA |
| Column | Acquity UPLC BEH C18 1.7 µm |

EXAMPLE 3002
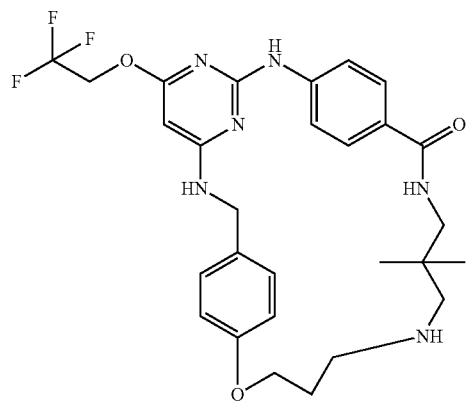
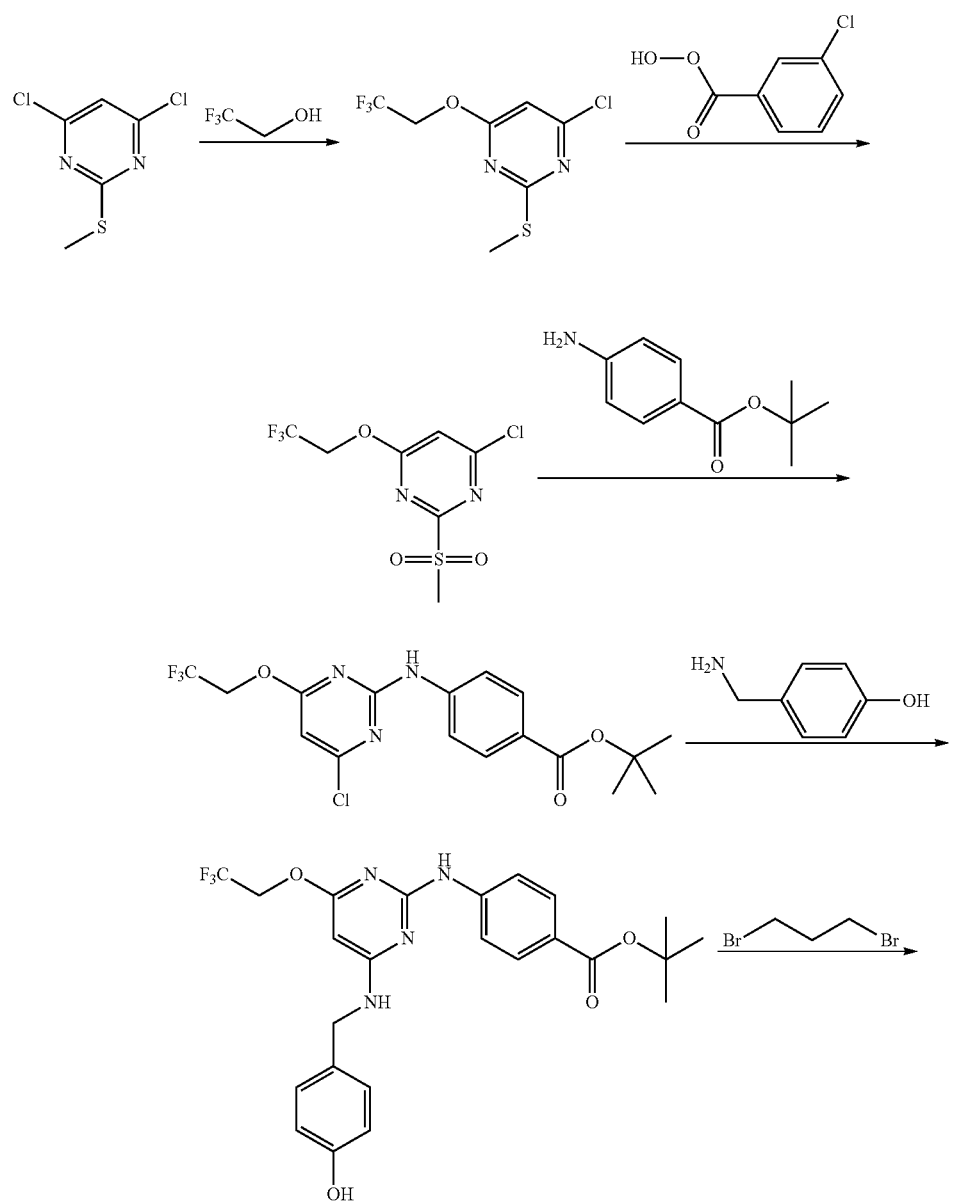

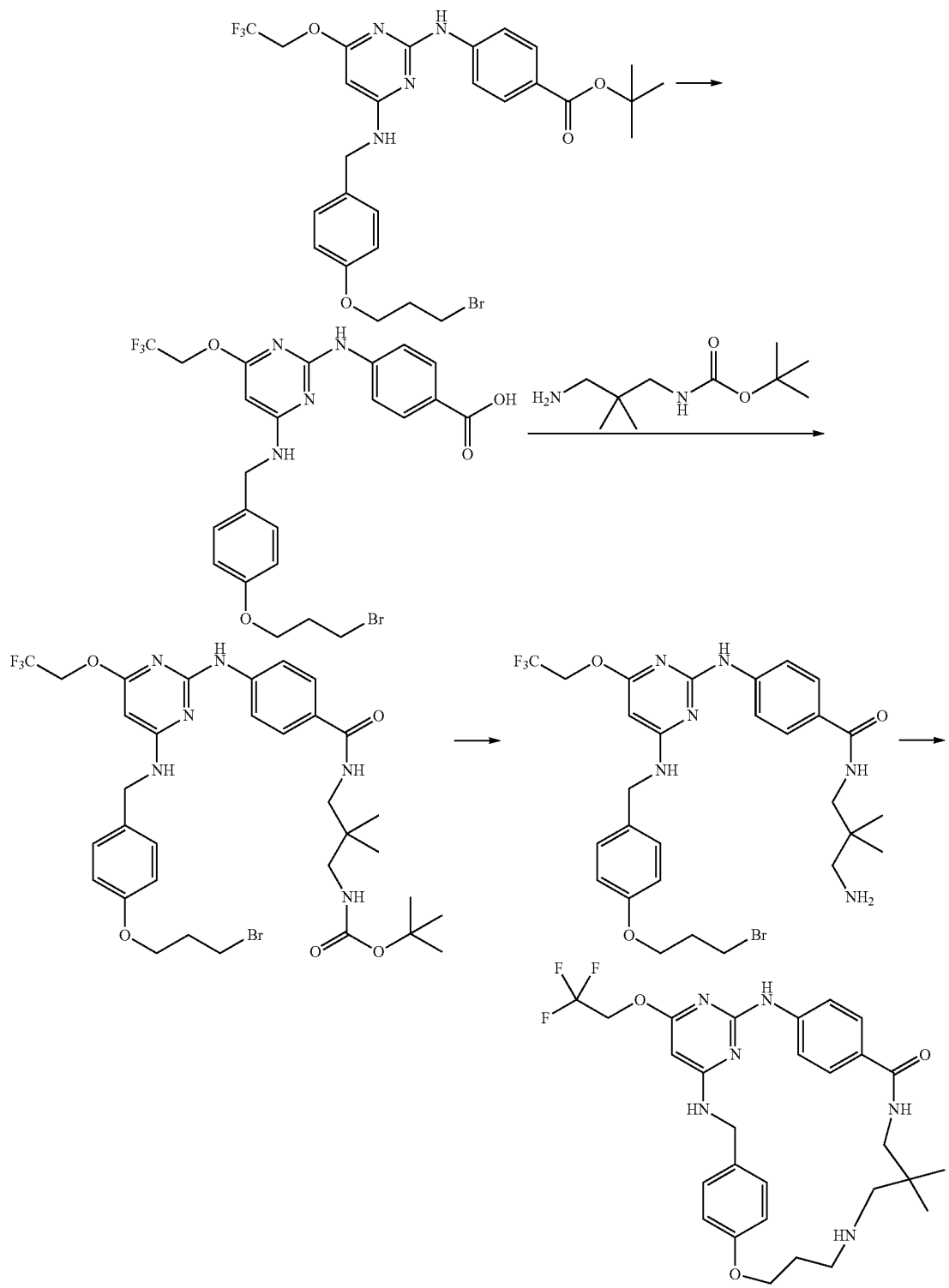

Step 1: To a solution of NaH (0.57 g, 14.35 mmol) in THF (10 mL) at 0° C. was added 2,2,2-trifluoroethanol (1.231 g, 12.30 mmol) dropwise. The mixture was stirred at 0° C. for 10 mins. The resulting mixture was transferred to the solution of 4,6-dichloro-2-(methylthio)pyrimidine (2 g, 10.25 mmol) in THF at 0° C. dropwise. Run the reaction for 16 hs at r.t. The reaction mixture was quenched with water, extracted with ethyl acetate, dried over Na$_2$SO$_4$, concentrated to give a crude product (3 g) that was used in the next step without purification.

| 4-chloro-2-(methylthio)-6-(2,2,2-trifluoroethoxy)pyrimidine | |
| --- | --- |
| MS (M + H)+ Calcd. | 259.6 |
| MS (M + H)+ Observ. | 259.0 |
| Retention Time | 2.16 min |
| LC Condition | |
| Solvent A | 95% Water-5% Methanol-10 mM Ammonium Actetate |
| Solvent B | 5% Water-95% Methanol-10 mM Ammonium Actetate |
| Start % B | 0 |
| Final % B | 100 |
| Gradient/Stop Time | 2 min/3 min |
| Flow Rate | 1 mL/min |
| Wavelength | 220 |
| Solvent Pair | Water-Methanol-Ammonium Actetate |
| Column | PHENOMENEX-LUNA 2.0 × 30 mm C18 3 μM |

Step 2: To a suspension of 4-chloro-2-(methylthio)-6-(2,2,2-trifluoroethoxy)pyrimidine (500 mg, 1.93 mmol) in DCM (10 mL) was added 3-chlorobenzoperoxoic acid (1.0 g, 4.83 mmol) at 0° C. The mixture was stirred at r.t for 16 hs. The reaction mixture was concentrated to give a crude material that was purified by Biotage eluting with 20% of ethyl acetate/hexane to give 385 mg (68.5%) of the desired product as a solid.

| 4-chloro-2-(methylsulfonyl)-6-(2,2,2-trifluoroethoxy)pyrimidine | |
| --- | --- |
| MS (M + H)+ Calcd. | 291.6 |
| MS (M + H)+ Observ. | 291.1 |
| Retention Time | 1.68 min |
| LC Condition | |
| Solvent A | 95% Water-5% Methanol-10 mM Ammonium Actetate |
| Solvent B | 5% Water-95% Methanol-10 mM Ammonium Actetate |
| Start % B | 0 |
| Final % B | 100 |
| Gradient/Stop Time | 2 min/3 min |
| Flow Rate | 1 mL/min |
| Wavelength | 220 |
| Solvent Pair | Water-Methanol-Ammonium Actetate |
| Column | PHENOMENEX-LUNA 2.0 × 30 mm C18 3 μM |

Step 3: To a mixture of 4-chloro-2-(methylsulfonyl)-6-(2,2,2-trifluoroethoxy)pyrimidine (100 mg, 0.34 mmol) and tert-butyl 4-aminobenzoate (80 mg, 0.41 mmol) in THF (5 mL) solution was added sodium bis(trimethylsilyl)amide 1 M in THF (0.69 mL, 0.69 mmol) solution. The resulting mixture was stirred at r.t for 16 h. The reaction mixture was quenched with water, extracted with ethyl acetate, dried over MgSO4, concentrated to give a crude material that was purified by Biotage eluting with 20% of ethyl acetate/hexane to give 30 mg (22%) of the desired product as a solid.

| tert-butyl 4-((4-chloro-6-(2,2,2-trifluoroethoxy)pyrimidin-2-yl)amino)benzoate | |
| --- | --- |
| MS (M + H)+ Calcd. | 404.1 |
| MS (M + H)+ Observ. | 404.0 |
| Retention Time | 1.19 min |
| LC Condition | |
| Solvent A | 100% Water: 0.05% TFA |
| Solvent B | 100% ACN: 0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN: Water: TFA |
| Column | Acquity UPLC BEH C18 1.7 μm |

Step 4: To a solution of tert-butyl 4-((4-chloro-6-(2,2,2-trifluoroethoxy)pyrimidin-2-yl)amino)benzoate (30 mg, 0.07 mmol), and Hunig's Base (0.026 mL, 0.15 mmol) in THF (1 mL) was added 4-(aminomethyl)phenol (33 mg, 0.27 mmol). The resulting mixture was stirred at 120° C. for 30 hs. The solvent was removed and the crude product was purified by silica gel chromatography using 20% -40% of EtOAc/Hexanes to give tert-butyl 4-((4-((4-hydroxybenzyl)amino)-6-(2,2,2-trifluoroethoxy)pyrimidin-2-yl)amino)benzoate (27 mg, 74%) as white solid.

| tert-butyl 4-((4-((4-hydroxybenzyl)amino)-6-(2,2,2-trifluoroethoxy)pyrimidin-2-yl)amino)benzoate | |
| --- | --- |
| MS (M + H)+ Calcd. | 491.2 |
| MS (M + H)+ Observ. | 491.1 |
| Retention Time | 1.07 min |
| LC Condition | |
| Solvent A | 100% Water: 0.05% TFA |
| Solvent B | 100% ACN: 0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN: Water: TFA |
| Column | Acquity UPLC BEH C18 1.7 μm |

Step 5: To a solution of tert-butyl 4-((4-((4-hydroxybenzyl)amino)-6-(2,2,2-trifluoroethoxy)pyrimidin-2-yl)amino)benzoate (27 mg, 0.06 mmol), 1,3-dibromoproane (33 mg, 0.17 mmol) in acetone (1 mL) was added potassium carbonate (23 mg, 0.17 mmol). The resulting solution was stirred for 16 h at reflux. After cooling to rt, the solvent was removed and the crude product was purified by Biotage eluting with 20% ethyl acetate in hexane to give tert-butyl 4-((4-((4-(3-bromopropoxy)benzyl)amino)-6-(2,2,2-trifluoroethoxy)pyrimidin-2-yl)amino)benzoate (34 mg, 100%) as white solid.

| tert-butyl 4-((4-((4-(3-bromopropoxy)benzyl)amino)-6-(2,2,2-trifluoroethoxy)pyrimidin-2-yl)amino)benzoate | |
| --- | --- |
| MS (M + H)+ Calcd. | 612.5 |
| MS (M + H)+ Observ. | 612.1 |
| Retention Time | 1.20 min |
| LC Condition | |
| Solvent A | 100% Water: 0.05% TFA |
| Solvent B | 100% ACN: 0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN: Water: TFA |
| Column | Acquity UPLC BEH C18 1.7 μm |

Step 6: Tert-butyl 4-((4-((4-(3-bromopropoxy)benzyl)amino)-6-(2,2,2-trifluoroethoxy)pyrimidin-2-yl)amino)benzoate (34 mg, 0.06 mmol) and 4 N HCl in dioxane (1 mL) were stirred for 8 hs then concentrated under vacuum to give 4-((4-((4-(3-bromopropoxy)benzyl)amino)-6-(2,2,2-trifluoroethoxy)pyrimidin-2-yl)amino)benzoic acid (31 mg, 0.06 mmol) which was carried to the next step without purification.

| 4-((4-((4-(3-bromopropoxy)benzyl)amino)-6-(2,2,2-trifluoroethoxy)pyrimidin-2-yl)amino)benzoic acid | |
|---|---|
| MS (M + H)+ Calcd. | 556.3 |
| MS (M + H)+ Observ. | 556.0 |
| Retention Time | 1.04 min |
| LC Condition | |
| Solvent A | 100% Water: 0.05% TFA |
| Solvent B | 100% ACN: 0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN: Water: TFA |
| Column | Acquity UPLC BEH C18 1.7 μm |

Step 7: To a solution of 4-((4-((4-(3-bromopropoxy)benzyl)amino)-6-(2,2,2-trifluoroethoxy)pyrimidin-2-yl)amino)benzoic acid (31 mg, 0.06 mmol), Hunig's Base (0.049 mL, 0.28 mmol) and tert-butyl (3-amino-2,2-dimethylpropyl)carbamate (22.6 mg, 0.11 mmol) in CH$_2$Cl$_2$ (2 mL) was added HATU (32 mg, 0.08 mmol). After stirring at room temperature for 1 h, the mixture was concentrated and purified by Biotage eluting with 50-70% ethyl acetate in hexane to give 35 mg of product (85%) as a white solid.

| tert-butyl (3-(4-((4-((4-(3-bromopropoxy)benzyl)amino)-6-(2,2,2-trifluoroethoxy)pyrimidin-2-yl)amino)benzamido)-2,2-dimethylpropyl)carbamate | |
|---|---|
| MS (M + H)+ Calcd. | 740.6 |
| MS (M + H)+ Observ. | 740.3 |
| Retention Time | 1.15 min |
| LC Condition | |
| Solvent A | 100% Water: 0.05% TFA |
| Solvent B | 100% ACN: 0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN: Water: TFA |
| Column | Acquity UPLC BEH C18 1.7 μm |

Step 8: tert-butyl (3-(4-((4-((4-(3-bromopropoxy)benzyl)amino)-6-(2,2,2-trifluoroethoxy)pyrimidin-2-yl)amino)benzamido)-2,2-dimethylpropyl)carbamate (35 mg, 0.047 mmol) was stirred in TFA/DCM (1:1) solution (2 mL) for 1 h. The solution was concentrated and free TFA to give N-(3-amino-2,2-dimethylpropyl)-4-((4-((4-(3-bromopropoxy)benzyl)amino)-6-(2,2,2-trifluoroethoxy)pyrimidin-2-yl)amino)benzamide (31 mg, 84%) which was carried to the next step without purification.

| N-(3-amino-2,2-dimethylpropyl)-4-((4-((4-(3-bromopropoxy)benzyl)amino)-6-(2,2,2-trifluoroethoxy)pyrimidin-2-yl)amino)benzamide | |
|---|---|
| MS (M + H)+ Calcd. | 640.5 |
| MS (M + H)+ Observ. | 641.2 |
| Retention Time | 0.95 min |
| LC Condition | |
| Solvent A | 100% Water: 0.05% TFA |
| Solvent B | 100% ACN: 0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN: Water: TFA |
| Column | Acquity UPLC BEH C18 1.7 μm |

Step 9: To a solution of N-(3-amino-2,2-dimethylpropyl)-4-((4-((4-(3-bromopropoxy)benzyl)amino)-6-(2,2,2-trifluoroethoxy)pyrimidin-2-yl)amino)benzamide (30 mg, 0.06 mmol) in ACN (2 mL) was added potassium carbonate (10 mg, 0.07 mmol). The mixture was heated in microwave reactor at 130° C. for 1 h. After cooling to rt, the mixture was filtered and white solid was washed with ACN. Pre-HPLC separation to give Compound 3002 (7.7 mg, 24%) as white solid.

$^1$H NMR (400 MHz, METHANOL-d$_4$) δ7.45-7.41 (d, J=9.0 Hz, 2H), 7.39-7.34 (d, J=9.3 Hz, 2H), 7.27-7.22 (d, J=8.8 Hz, 2H), 6.99-6.94 (d, J=8.8 Hz, 2H), 5.0 (s, 1H), 4.84 (q, J=8.8 Hz, 2H), 4.60 (s, 2H), 4.42 (t, J=5.8 Hz, 2H), 3.36 (s, 2H), 3.12 (t, J=6.0 Hz, 2H), 2.65 (s, 2H), 2.34-2.22 (m, 2H), 1.11 (s, 6H).

| Compound 3002 | |
|---|---|
| MS (M + H)+ Calcd. | 559.6 |
| MS (M + H)+ Observ. | 559.1 |
| Retention Time | 0.88 min |
| LC Condition | |
| Solvent A | 100% Water: 0.05% TFA |
| Solvent B | 100% ACN: 0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN: Water: TFA |
| Column | Acquity UPLC BEH C18 1.7 μm |

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

We claim:
1. A compound of formula I

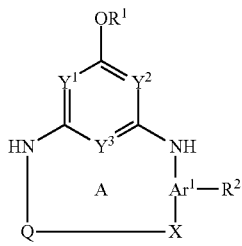

where
- $Y^1$ and $Y^3$ are N and $Y^2$ is CH or $Y^2$ and $Y^3$ are N and $Y^1$ is CH;
- $Ar^1$ is phenyl or pyridinyl substituted with 1 $R^2$;
- $R^1$ is alkyl, hydroxyalkyl, alkoxyalkyl, haloalkyl, cycloalkyl, hydroxycycloalkyl, alkoxycycloalkyl, halocycloalkyl, cycloalkenyl, benzyl, indanyl, or alkylcarbonyl;
- $R^2$ is hydrogen, cyano, halo, alkyl, haloalkyl, alkoxy, or haloalkoxy;
- $R^3$ is hydrogen, alkyl, (amino)alkyl, (alkylamino)alkyl, (dialkylamino)alkyl, ((alkylcarbonyl)amino)alkyl, ((haloalkylcarbonyl)amino)alkyl, ((alkoxycarbonyl)amino)alkyl, ((benzyloxycarbonyl)amino)alkyl, alkylcarbonyl, alkoxycarbonyl, benzyloxycarbonyl, aminocarbonyl, alkylaminocarbonyl, or dialkyaminocarbonyl;
- $R^4$ is hydrogen, alkyl, (amino)alkyl, (alkylamino)alkyl, or (dialkylamino)alkyl;
- $R^5$ is hydrogen, alkyl, (amino)alkyl, (alkylamino)alkyl, or (dialkylamino)alkyl;
- Q is an alkylene or alkenylene chain containing 0-6 groups selected from the group consisting of O, $NR^3$, S, S(O), S($O_2$), C(O)O, C(O)$NR^4$, OC(O)$NR^4$, $NR^4$C(O)$NR^4$, and Z, provided that any O or S atom does not directly bond to another O or S atom, such that ring A is 13-36 membered; and where the alkylene or alkenylene chain is substituted with 0-6 substituents selected from the group consisting of alkyl, alkylene, hydroxy, and alkoxy;
- X is O, $CH_2$, CO, $CO_2$, or C(O)$NR^5$; and
- Z is $C_{3-7}$ cycloalkylene or phenylene;
or a pharmaceutically acceptable salt thereof.

2. A compound of claim 1 where
- $Ar^1$ is phenyl or pyridinyl substituted with 1 $R^2$;
- $R^1$ is haloalkyl;
- $R^2$ is hydrogen or halo;
- $R^3$ is hydrogen or alkyl;
- $R^5$ is hydrogen or alkyl;
- Q is an alkylene or alkenylene chain containing 0-6 groups selected from the group consisting of O, $NR^3$, and Z, provided that any O atom does not directly bond to another O atom, such that ring A is 13-36 membered; and where the alkylene or alkenylene chain is substituted with 0-6 substituents selected from the group consisting of alkyl and alkylene;
- X is C(O)$NR^5$; and
- Z is $C_{3-7}$ cycloalkylene or phenylene;
or a pharmaceutically acceptable salt thereof.

3. A compound of claim 1 where
- $Ar^1$ is 1,4-benzenediyl or 1,4-dipyridindiyl substituted with 1 $R^2$;
- $R^1$ is trifluoroethyl;
- $R^2$ is hydrogen or fluoro;
- $R^3$ is hydrogen;
- $R^5$ is hydrogen;
- Q is an alkylene or alkenylene chain containing 0-6 groups selected from the group consisting of O, $NR^3$, and Z, provided that any O atom does not directly bond to another O atom, such that ring A is 13-36 membered; and where the alkylene or alkenylene chain is substituted with 0-6 substituents selected from the group consisting of methyl and methylene;
- X is C(O)$NR^5$; and
- Z is $C_{3-7}$ cycloalkylene or phenylene;
or a pharmaceutically acceptable salt thereof.

4. A compound of claim 1 where $Ar^1$ is 1,4-benzenediyl substituted with 1 $R^2$; or a pharmaceutically acceptable salt thereof.

5. A compound of claim 1 where $Ar^1$ is 1,4-dipyridindiyl substituted with 1 $R^2$; or a pharmaceutically acceptable salt thereof.

6. A compound of claim 1 where Z is 1,4-phenylene; or a pharmaceutically acceptable salt thereof.

7. A compound of claim 1 where Z is cyclopropylene; or a pharmaceutically acceptable salt thereof.

8. A compound of claim 1 selected from the group consisting of

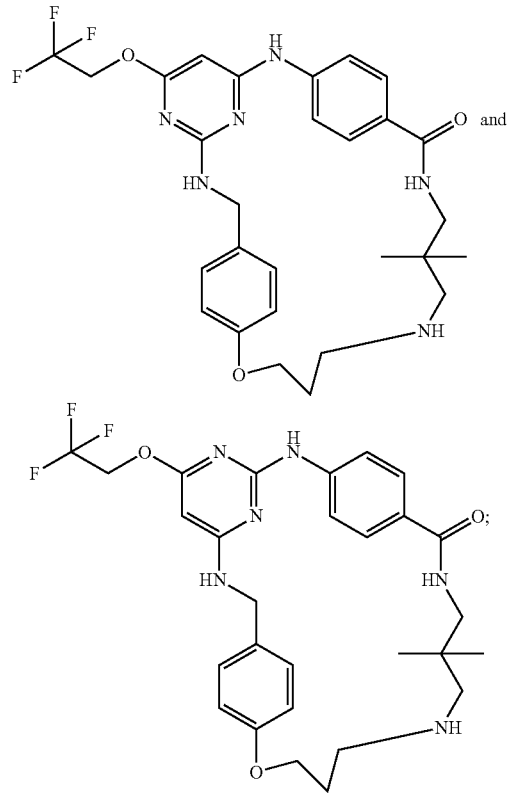

or a pharmaceutically acceptable salt thereof.

9. A composition comprising a compound of claim 1, or a pharmaceutically acceptable salt thereof, and a pharmaceutically acceptable carrier.

10. The composition of claim 9 further comprising at least one additional compound having therapeutic benefits for HCV wherein the compound is selected from the group consisting of interferons, cyclosporins, interleukins, HCV metalloprotease inhibitors, HCV serine protease inhibitors, HCV polymerase inhibitors, HCV helicase inhibitors, HCV NS4B protein inhibitors, HCV entry inhibitors, HCV assembly inhibitors, HCV egress inhibitors, HCV NS5A protein inhibitors, HCV NS5B protein inhibitors, and HCV replicon inhibitors.

11. A method of treating hepatitis C infection comprising administering a therapeutically effective amount of a compound of claim 1 to a patient.

12. The method of claim 11 further comprising administering at least one additional compound having therapeutic benefits for HCV wherein the compound is selected from the group consisting of interferons, cyclosporins, interleukins, HCV metalloprotease inhibitors, HCV serine protease inhibitors, HCV polymerase inhibitors, HCV helicase inhibitors, HCV NS4B protein inhibitors, HCV entry inhibitors, HCV assembly inhibitors, HCV egress inhibitors, HCV NS5A protein inhibitors, HCV NS5B protein inhibitors, and HCV replicon inhibitors.

* * * * *

UNITED STATES PATENT AND TRADEMARK OFFICE
CERTIFICATE OF CORRECTION

| | | |
|---|---|---|
| PATENT NO. | : 8,697,706 B2 | Page 1 of 1 |
| APPLICATION NO. | : 13/628529 | |
| DATED | : April 15, 2014 | |
| INVENTOR(S) | : Li-Qiang Sun et al. | |

It is certified that error appears in the above-identified patent and that said Letters Patent is hereby corrected as shown below:

In the Specification:

Column 7, line 27, change "Imiqimod," to -- Imiquimod, --.

Column 7, line 27, change "5′-monophospate" to -- 5′-monophosphate --.

Column 8, line 9, change "Imiqimod," to -- Imiquimod, --.

Column 8, line 10, change "5′-monophospate" to -- 5′-monophosphate --.

In the Claims:

Claim 1:

Column 31, line 32, change "dialkyaminocarbonyl;" to -- dialkylaminocarbonyl; --.

Signed and Sealed this
Thirty-first Day of March, 2015

Michelle K. Lee
*Director of the United States Patent and Trademark Office*